United States Patent
Arisawa et al.

(10) Patent No.: US 10,287,260 B2
(45) Date of Patent: May 14, 2019

(54) COMPOSITE CONTAINING CATALYTIC METAL NANOPARTICLES, AND USE FOR SAME

(71) Applicants: Japan Science and Technology Agency, Kawaguchi-shi, Saitama (JP); Furuya Metal Co., Ltd., Tokyo (JP)

(72) Inventors: Mitsuhiro Arisawa, Suita (JP); Satoshi Shuto, Hokkaido (JP); Naoyuki Hoshiya, Hokkaido (JP); Satoshi Arai, Tokyo (JP)

(73) Assignees: Japan Science and Technology Agency, Kawaguchi-shi, Saitama (JP); Furuya Metal Co., Ltd., Tokyo (JP)

( * ) Notice: Subject to any disclaimer, the term of this patent is extended or adjusted under 35 U.S.C. 154(b) by 438 days.

(21) Appl. No.: 14/780,616

(22) PCT Filed: Mar. 28, 2014

(86) PCT No.: PCT/JP2014/059312
§ 371 (c)(1),
(2) Date: Jan. 19, 2016

(87) PCT Pub. No.: WO2014/157677
PCT Pub. Date: Oct. 2, 2014

(65) Prior Publication Data
US 2016/0152583 A1 Jun. 2, 2016

(30) Foreign Application Priority Data
Mar. 28, 2013 (JP) ................. 2013-069471

(51) Int. Cl.
| | | |
|---|---|---|
| *B01J 23/44* | (2006.01) | |
| *B01J 23/46* | (2006.01) | |
| *B01J 23/52* | (2006.01) | |
| *B01J 23/75* | (2006.01) | |
| *B01J 31/06* | (2006.01) | |
| *B01J 31/16* | (2006.01) | |
| *B01J 31/28* | (2006.01) | |
| *B01J 35/00* | (2006.01) | |
| *B82Y 30/00* | (2011.01) | |

(Continued)

(52) U.S. Cl.
CPC .......... *C07D 295/033* (2013.01); *B01J 23/44* (2013.01); *B01J 23/462* (2013.01); *B01J 23/464* (2013.01); *B01J 23/468* (2013.01); *B01J 23/52* (2013.01); *B01J 23/745* (2013.01); *B01J 23/75* (2013.01); *B01J 23/755* (2013.01); *B01J 31/06* (2013.01); *B01J 31/28* (2013.01); *B01J 35/002* (2013.01); *B01J 35/006* (2013.01); *B01J 35/0013* (2013.01); *B82Y 30/00* (2013.01); *C07B 37/04* (2013.01); *C07D 295/023* (2013.01); *B01J 31/165* (2013.01); *B01J 2231/4205* (2013.01); *B01J 2231/4211* (2013.01); *B01J 2231/4255* (2013.01); *B01J 2231/4261* (2013.01); *B01J 2231/4266* (2013.01); *B01J 2231/4283* (2013.01)

(58) Field of Classification Search
CPC ............................... B01J 23/44; B01J 23/755
See application file for complete search history.

(56) References Cited

U.S. PATENT DOCUMENTS

| | | | |
|---|---|---|---|
| 2008/0020923 A1* | 1/2008 | Debe ................. | B01J 23/42 502/100 |
| 2012/0115714 A1 | 5/2012 | Arisawa et al. | |

FOREIGN PATENT DOCUMENTS

| | | |
|---|---|---|
| CN | 101263620 A | 9/2008 |
| CN | 101501918 A | 8/2009 |

(Continued)

OTHER PUBLICATIONS

Perez-Lorenzo "Palladium Nanoparticles as Efficient Catalysts for Suzuki Cross-Coupling Reactions" J. Phys. Chem. Lett., 2012, 3 (2), pp. 167-174.*

(Continued)

*Primary Examiner* — Joseph R Kosack
(74) *Attorney, Agent, or Firm* — Panitch Schwarze Belisario & Nadel LLP

(57) ABSTRACT

Provided is a material that, when compared with SAPd, exhibits the similar activity in cross-coupling (CC) reactions, can decrease the amount of catalytic metal that is mixed into the reaction product, and increases the number of times use can be repeated. Provided are a catalyst and a catalyst precursor that use a catalytic metal other than Pd and that exhibit the CC reaction activity similar to when Pd is used. Provided are a catalyst and a catalyst precursor that exhibit the similar CC reaction activity when using Pd or a catalytic metal other than Pd, without using a carrier such as metal and without using piranha solution. A composite wherein catalytic metal nanoparticles are dispersed in a continuous phase comprising a polymer having C2-6 alkylene group units and phenylene group units (an alkylene group unit being bonded to at least the first and fourth position of the phenylene group unit). The particle diameter of the catalytic metal nanoparticles is at most 20 nm. A composite structure including a substrate, and the aforementioned composite provided to the surface of the substrate. A method for manufacturing the composite structure by dehydrocondensating, in the presence of a catalytic metal compound, a benzene compound having at least two alkyl groups (two of the alkyl groups being at the first and fourth position) in order to form the composite on the substrate surface.

20 Claims, 11 Drawing Sheets

(51) Int. Cl.
*C07B 37/04* (2006.01)
*B01J 23/745* (2006.01)
*B01J 23/755* (2006.01)
*C07D 295/023* (2006.01)
*C07D 295/033* (2006.01)

(56) References Cited

FOREIGN PATENT DOCUMENTS

| | | |
|---|---|---|
| EP | 2457656 A1 | 5/2012 |
| JP | S42005023 Y1 | 3/1967 |
| JP | 2006205105 A | 8/2006 |
| JP | 2009509776 A | 3/2009 |
| JP | 2009541963 A | 11/2009 |
| JP | 201628795 A | 3/2016 |
| WO | 2007032864 A2 | 3/2007 |
| WO | 2008000709 A1 | 1/2008 |
| WO | 2011010610 A1 | 1/2011 |
| WO | 2011121017 A1 | 10/2011 |

OTHER PUBLICATIONS

Balanta et al., "Pd nanoparticles for C—C coupling reactions," Chem. Soc. Rev., vol. 40, pp. 4973-4985 (2011).

Hoshiya et al., "Sulfur Modification of Au via Treatment with Piranha Solution Provides Low-Pd Releasing and Recyclable Pd Material, SAPd," J. Am. Chem. Soc., vol. 132, pp. 7270-7272 (2010).

Hoshiya et al., "The Actual Active Species of Sulfur-Modified Gold-Supported Palladium as a Highly Effective Palladium Reservoir in the Suzuki-Miyaura Coupling," Adv. Synth. Catal., vol. 353, pp. 743-748 (2011).

International Search Report and Written Opinion dated Sep. 22, 2014 in International Application No. PCT/JP2014/059312.

International Preliminary Report on Patentability dated Apr. 28, 2015 in International Application No. PCT/JP2014/059312.

Office Action dated Aug. 23, 2016 in JP Application No. 2013-069471.

Office Action dated Aug. 29, 2017 in JP Application No. 2016-114920.

Extended Search Report dated Jan. 10, 2017 in EP Application No. 14774636.6.

Office Action dated Jan. 20, 2017 in KR Application No. 10-2015-7031059.

Office Action dated Jan. 22, 2017 in CN Application No. 201480018494.4.

Al-Amin et al, "Development of Second Generation Gold-Supported Palladium Material with Low-Leaching and Recyclable Characteristics in Aromatic Amination," The Journal of Organic Chemistry, vol. 78, pp. 7575-7581 (2013).

Astruc at al, "Nanoparticles as Recyclable Catalysts: The Frontier between Homogeneous and Heterogeneous Catalysis," Angewandte Chemie Int'l Ed. 44, pp. 7852-7872 (2005).

Park et al, "Electrical Characteristics of Gold Nanoparticle-Embedded MIS Capacitors with Parylene Gate Dielectric," Organix Electronics, vol. 9, No. 5, pp. 878-882 (2008).

Office Action dated Jun. 5, 2018 in JP Application No. 2016-114920.

\* cited by examiner

- SAPd : SAPd before reaction
- SAPd SM after: SAPd after 10 cycles of Suzuki-Miyaura coupling
- SAPd BH after: SAPd after 10 cycles of Buchwald-Hartwig coupling

|  | r (Å) | N | D (nm) |
|---|---|---|---|
| Pd foil | 2.74 | 12 | — |
| PdNSXP before | 2.79 | 9.1 | 3 |
| PdNSXP BH after | 2.80 | 8.1 | 2 |

- PdNSXP : PdNSXP before reactions
- AuS: sulfur-modifed Au

COMPOSITE CONTAINING CATALYTIC METAL NANOPARTICLES, AND USE FOR SAME

TECHNICAL FIELD

The present invention relates to a composite containing catalytic metal nanoparticles and to the use thereof.

CROSS-REFERENCE TO RELATED APPLICATIONS

This application claims priority to Japanese Patent Application No. 2013-69471 filed on Mar. 28, 201, which is expressly incorporated herein by reference in its entirety.

BACKGROUND ART

Because palladium catalysts are important in carbon-carbon (hetero element) bond-forming reactions, palladium nanoparticle (PdNp) catalysts and reactions employing them have been reported over the past decade (for example, Nonpatent Reference 1). In PdNp catalysts, the surface area of the nanoparticles (Np) is broader and more active than in bulk catalysts. As a result, they are characterized as reactions that progress under mild and environmentally-friendly conditions. For example, it has recently been progressively found that traditional reactions that progress using 0 valence/divalent palladium catalysts in the presence of ligands, including phosphine ligands and nitrogen-containing heterocyclic carbene (NHC), can progress ligand free when employing PdNp. Thus, there are numerous advantages, not just in terms of cost, but also in terms of post-processing and product purification. Particularly in the areas of pharmaceutical and functional molecule synthesis, it is thought that their importance will continue to increase beyond what it is today.

The method of manufacturing the above metal Np utilizes polymers and ionic liquids (Nonpatent Reference 1).

The present inventors have successfully developed sulfur-modified Au-supported Pd catalysts (SAPd). When employing an SAPd, by repeatedly conducting (several hundred to several thousand times) ligand-free Pd cross-coupling (Suzuki-Miyaura coupling, a carbon-carbon bond-forming reaction, and the Buchwald-Hartwig reaction, a carbon-nitrogen bond-forming reaction), the quantity of Pd leakage in the reaction solution is on the order of 10 to 100 ppb (Nonpatent References 2 and 3, Patent Reference 1). This is the first example of an SAPd that permits a ligand free Buchwald-Hartwig reaction.

[Patent Reference 1] WO2011/010610 and US2012/0115714

[Nonpatent Document 1] A. Balanta, C. Godard and C. Claver, *Chem. Soc. Rev.* 2011, 40, 4973.

[Nonpatent Document 2] *J. Am. Chem. Soc.* 2010, 132, 7270-7272.

[Nonpatent Document 3] *Adv. Synth. Catal.* 2011, 353, 743-748.

SUMMARY OF THE INVENTION

Problem to be Solved by the Invention

The surface of the SAPd described in Patent Reference 1 comprises an elemental sulfur-modified gold or gold alloy structure and a catalytic metal compound supported by this structure. In photoelectron spectroscopy, in addition to the peak derived from the catalytic metal compound, sulfur in the form of the sulfur 1 s orbital peak is described as a catalyst precursor observed in the 2,470 eV±2 eV range at the peak top position (claim 1). However, the catalytic metal compound is, for example, a complex or salt of Pd (claim 6).

The SAPd described in Nonpatent Reference 2 and Patent Reference 1 is a catalyst precursor that exhibits good catalytic performance in Pd cross-coupling reactions. This catalyst precursor releases Pd in solvent, supplying it to cross-coupling reactions. When the temperature of the solvent is returned to the vicinity of ordinary temperature once the reaction has ended, the Pd that has been released is picked up by the catalyst precursor, making it recyclable. However, the number of times it can be recycled, while also depending on the type of catalyst precursor, is about 10 to 30.

The first object of the present invention is to provide a material in the form of a catalyst precursor or catalyst in which nanoparticles of a catalytic metal such as Pd have been immobilized in the manner similar to the SAPd described in Nonpatent Reference 2 and Patent Reference 1 that can increase the number of times the catalyst or catalyst precursor can be repeatedly used, reduce the quantity of catalytic metal nanoparticles mixing into the reaction product, and suppress the quantity of catalytic metal nanoparticles leaching into the reaction solvent, while affording cross-coupling reaction activity that is equivalent to that of the SAPd described in Nonpatent Reference 2 and Patent Reference 1.

A further object of the present invention is to provide a catalyst, or catalyst precursor, having the cross-coupling reaction activity similar to Pd when employing a catalytic metal other than Pd.

In Nonpatent Reference 2 and Patent Reference 1, gold or a gold alloy is employed as a carrier. A further object of the present invention is to provide a catalyst, or catalyst precursor, having the similar cross-coupling reaction activity using Pd and a catalytic metal other than Pd without employing gold or a gold alloy as a carrier.

In Nonpatent Reference 2 and Patent Reference 1, the catalyst is prepared with a gold or gold alloy carrier employing a piranha solution. However, a piranha solution is an extremely corrosive solution. Further, each time a piranha solution is used, it must be prepared from hydrogen peroxide and concentrated sulfuric acid. It does not lend itself to large-quantity production. Thus, it is desirable to be able to prepare the catalyst without using a piranha solution. According, a further object of the present invention is to provide a catalyst, or catalyst precursor, affording the similar cross-coupling reaction activity using Pd and catalytic metals other than Pd without using a piranha solution.

A still further object of the present invention is to provide a method for manufacturing a coupling product employing a catalyst, or catalyst precursor, having this coupling reaction activity.

Means of Solving the Problem

The present invention is as set forth below.

[1]

A composite in which catalytic metal nanoparticles are dispersed in a continuous phase comprised of a polymer with a phenylene group unit and an alkylene group unit having a number of carbon atoms ranging from 2 to 6, wherein the alkylene group unit is bonded to the phenylene group unit in at least positions 1 and 4, and wherein at least a portion of the catalytic metal nanoparticles have a particle diameter of less than or equal to 20 nm.

[2]

The composite described in [1], wherein the polymer has a sulfate group cross-linkage.

[3]

The composite described in [2], wherein the sulfate group cross-linkage is present between alkylene group units.

[4]
The composite described in [2] or [3], wherein the content of the sulfate group cross-linkage falls within a range of 0.0001 to 0.1 as a molar ratio with the alkylene group units.
[5]
The composition described in any one of [1] to [4], wherein the number of carbon atoms in the alkylene group unit ranges from 2 to 4.
[6]
The composite described in any one of [1] to [5], wherein the alkylene group units are bonded to the phenylene group unit at positions 1, 2, and 4, or at positions 1, 2, 4, and 5.
[7]
The composite described in any one of [1] to [6], wherein the ratio of the mass of the continuous phase comprised of the polymer to the mass of the catalytic metal nanoparticles ranges from 100:0.1 to 100:10.
[8]
The composite described in any one of [1] to [7], wherein the catalytic metal constituting the catalytic metal nanoparticles is at least one metal selected from the group consisting of iron, nickel, cobalt, ruthenium, rhodium, palladium, iridium, platinum, and gold.
[9]
The composite described in any one of [1] to [7], wherein the catalytic metal nanoparticles are Pd nanoparticles at least a portion of which have a particle diameter falling within a range of 2 to 10 nm.
[10]
The composite described in any one of [1] to [7], wherein the catalytic metal nanoparticles are Ni nanoparticles at least a portion of which have a particle diameter falling within a range of 5 to 20 nm.
[11]
A composite structure comprising a substrate and the composite described in any one of [1] to [10] provided on at least a portion of the surface of the substrate.
[12]
The composite structure described in [11], wherein the substrate is metal, glass, ceramic, or resin.
[13]
A catalyst, or catalyst precursor, for a coupling reaction comprising the composite described in any one of [1] to [10] or the composite structure described in [11] or [12].
[14]
The catalyst or catalyst precursor described in [13] wherein the coupling reaction employs a halogenated hydrocarbon as at least a portion of the starting material or as an additive.
[15]
The catalyst or catalyst precursor described in [13] or [14] wherein the coupling reaction is a carbon-carbon bond-forming reaction or a carbon-nitrogen bond-forming reaction.
[16]
A method for manufacturing the composite structure described in [11], comprising subjecting a benzene compound having two or more alkyl groups, wherein two alkyl groups are at positions 1 and 4, to dehydrogenative condensation on a substrate surface in the presence of a catalytic metal compound to form the composite described in [1] to [10].
[17]
The manufacturing method described in [16], wherein the substrate is a substrate with a surface to which sulfur (S) has been bonded or adsorbed or a substrate with a surface to which sulfur (S) has not been bonded or adsorbed.
[18]
A method for manufacturing a coupling product comprising subjecting a plurality of organic compounds to a coupling reaction to obtain a coupling product with the composite described in any one of [1] to [10] or the composite structure described in [11] or [12].
[19]
The manufacturing method described in [18], wherein the coupling reaction employs a halogenated hydrocarbon as at least a portion of the starting material or as an additive.
[20]
The manufacturing method described in [18] or [19], wherein the coupling reaction is a carbon-carbon bond-forming reaction or a carbon-nitrogen bond-forming reaction.

Effect of the Invention

The present invention provides a material that can increase the number of times a catalyst or catalyst precursor can be repeatedly used, reduce the quantity of catalytic metal nanoparticles mixing into the reaction product, and suppress the quantity of catalytic metal nanoparticles leaching out into the reaction solvent, while affording cross-coupling reaction activity that is equivalent to that of a conventional SAPd. The present invention further provides a catalyst, or catalyst precursor, having cross-coupling reaction activity similar to when Pd is used, when using a catalytic metal other than Pd. Additionally, the present invention provides a catalyst, or catalyst precursor, having similar cross-coupling reaction activity using Pd and a catalytic metal other than Pd, without using gold or a gold alloy as a carrier. Further, the present invention provides a catalyst, or catalyst precursor, having similar cross-coupling reaction activity using Pd and a catalytic metal other than Pd, without using a piranha solution. Still further, the present invention provides a method for manufacturing a coupling product comprising using the composite or composite structure of the present invention to cause a plurality of organic compounds to undergo a coupling reaction yielding a coupling product.

MODES OF CARRYING OUT THE INVENTION

<The Composite>

Figure 1:
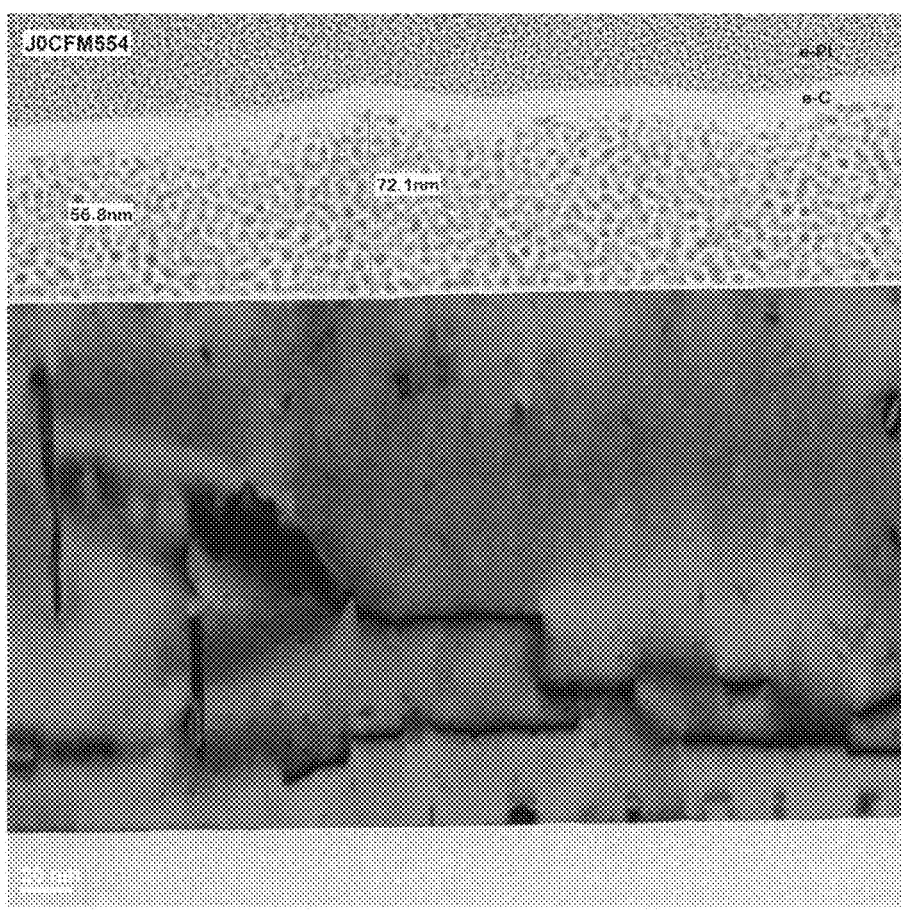
FIG. 1 A cross-sectional TEM image of the composite (PdNSXP) with substrate of the present invention obtained in Example 1.

The composite of the present invention is a composite in which catalytic metal nanoparticles are dispersed in a continuous phase comprised of a polymer with a phenylene group unit and a linear or branched chain alkylene group unit having a number of carbon atoms ranging from 2 to 6. The alkylene group unit is bonded to the phenylene group unit in at least positions 1 and 4. Further, at least a portion of the catalytic metal nanoparticles have a particle diameter of less than or equal to 20 nm.

The composite of the present invention is a composite in which catalytic metal nanoparticles are dispersed in a continuous phase comprised of a polymer.

The continuous phase is comprised of a polymer with a phenylene group unit and a linear or branched chain alkylene group unit having a number of carbon atoms ranging from 2 to 6. When the alkylene group unit is a linear chain, it can be an ethylene unit, n-propylene unit, n-butylene unit, n-pentylene unit, or n-hexylene unit. The linear alkylene group unit is desirably an ethylene unit or an n-butylene unit. When the alkylene group unit is a branched chain, it can be an iso-propylene unit with each end being bonded to respective three phenylene group units, or a 2-ethylbutylene unit in which each end is bonded to respective three phenylene group units. A linear alkylene group unit and a branched chain alkylene group unit can be present together in a single polymer. For example, an ethylene unit and an iso-propylene unit each end of which is bonded to respective three phenylene group units can be present together in a single polymer, and an n-butylene unit and a 2-ethylbutylene unit each end of which is bonded to respective three phenylene group units can be present together in a single polymer.

The alkylene group unit such as an ethylene unit and phenylene group unit are desirably present in alternating shifts.

The alkylene group unit is bonded to the phenylene group unit in at least positions 1 and 4. The alkylene group unit is desirably bonded to the phenylene group unit at positions 1 and 4. However, cases where the alkylene group unit is bonded to the phenylene group unit at positions 1, 2, and 4, or at positions 1, 2, 4, and 5, are also included in the composite of the present invention.

The polymer is obtained by polymerizing at least dialkyl-substituted benzene. In the case of dialkyl-substituted benzene, the alkyl groups of different dialkyl-substituted benzene molecules undergo dehydrogenative condensation to form alkylene groups, yielding a polymer. When the dialkyl-substituted benzene is, for example, dimethylbenzene, that is, xylene, the two methylenes present in two xylene molecules undergo dehydrogenative condensation to form ethylene groups, yielding a polymer. Alternatively, three methylenes on three xylene molecules undergo dehydrogenative condensation to form iso-propylene units in which each end is bonded to three phenylene group units, yielding a polymer. Because the formation of the polymer takes place in parallel with dispersion of the catalytic metal nanoparticles, this point will be described in detail.

In the polymer constituting the continuous phase of the composite of the present invention, the alkylene group unit is bonded to the phenylene group unit in at least positions 1 and 4. Due to this structure, when the composite of the present invention is employed as a catalyst or catalyst precursor, it affords desirable characteristics. These will be described farther below in detail.

The polymer constituting the continuous phase of the composite of the present invention can comprise a sulfate group cross-linkage. The sulfate group cross-linkage can be present between the alkylene group units. The content of the sulfate group cross-linkage can fall within a range of 0.0001 to 0.5 as a molar ratio with the alkylene group units. It desirably falls within a range of 0.001 to 0.3.

A schematic view of the polymer constituting the continuous phase of the composite of the present invention having a sulfate group cross-linkage is given below. However, the polymer in the present invention does not have the repeating unit of the schematic view given below. The goal of the schematic view given below is to schematically show the presence of a linear alkylene group unit, branched chain alkylene group unit, and sulfate group cross-linkage. It shows an example where an ethylene unit, an iso-propylene unit each end of which is bonded to respective three phenylene group units, and a sulfate group cross-linkage are present together in a single polymer.

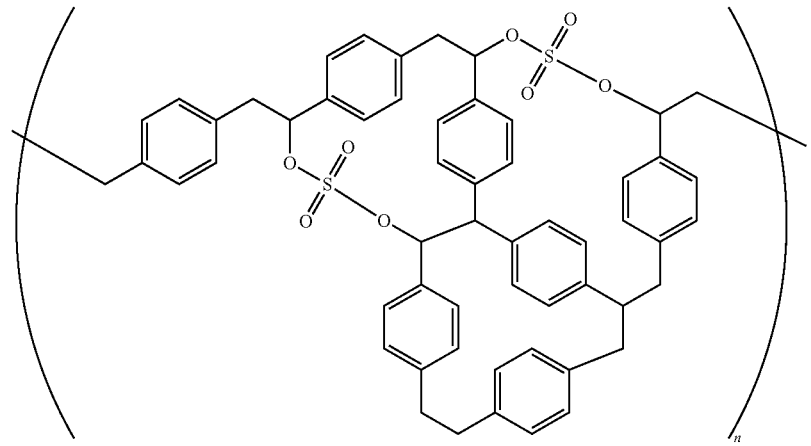

[Chem. 1]

It suffices for the catalytic metal constituting the catalytic metal nanoparticles dispersed in the continuous phase of the composite of the present invention to have catalytic activity for reactions used in organic synthesis, desirably reactions that form new bonds, and preferably, reactions that form new carbon-carbon bonds, new carbon-nitrogen bonds, or new carbon-oxygen bonds. Examples of such catalytic metals are the transition metals. Specific examples are at least one metal selected from the group consisting of iron, nickel, cobalt, ruthenium, rhodium, palladium, iridium, platinum, and gold. From the perspective of serving as a catalyst in a coupling reaction, desirable examples of catalytic metals are nickel, ruthenium, rhodium, iridium, palladium, platinum, and gold, and preferred examples are nickel, ruthenium, palladium, platinum, and gold.

At least a portion of the catalytic metal nanoparticles can have a particle diameter ranging from 2 to 20 nm. The particle diameter of the catalytic metal nanoparticles impacts catalytic activity in the coupling reaction and is desirably relatively fine. Accordingly, taking this perspective into account, at least a portion of the catalytic metal nanoparticles has a particle diameter ranging from 2 to 18 nm, preferably ranging from 2 to 16 nm, and more preferably, ranging from 2 to 15 nm. The range of the particle diameter can vary with the type of catalytic metal nanoparticle. For example, in the case of Pd nanoparticles, at least a portion can have a particle diameter ranging from 2 to 10 nm, desirably ranging from 2 to 8 nm. In the case of catalytic metal nanoparticles in the form of Ni nanoparticles, at least a portion can have a particle diameter ranging from 5 to 20 nm, desirably ranging from 10 to 18 nm. In the case of catalytic metal nanoparticles in the form of Ru nanoparticles, at least a portion can have a particle diameter ranging from 5 to 20 nm, desirably ranging from 10 to 18 nm, in the case of catalytic metal nanoparticles in the form of Pt nanoparticles, at least a portion can have a particle diameter ranging from 5 to 20 nm, desirably ranging from 10 to 18 nm, in the case of catalytic metal nanoparticles in the form of Au nanoparticles, at least a portion can have a particle diameter ranging from 5 to 20 nm, desirably ranging from 10 to 18 nm:

The ratio of the mass of the continuous phase comprised of polymer to the mass of catalytic metal nanoparticles is not specifically limited. However, taking into account catalytic activity and the like, the ratio falls for example within a range of from 100:0.1 to 100:10, desirably within a range of from 100:0.5 to 100:5. However, these ranges are not intended as limitations.

The present invention includes composite structures containing the composite of the present invention and a substrate having the composite on at least a portion of the surface thereof. From the perspective of maintaining the structure and facilitating handling, it is desirable for the continuous phase in the composite of the present invention to be formed on a suitable substrate. Examples of the substrate are metal, glass, ceramic, and resin. By way of example, the substrate can be in the form of a sheet, mesh, cylinder, coil, or particle, or in the form of some combination thereof.

<The Method for Manufacturing a Composite>

An example of manufacturing a composite structure by the method for manufacturing a composite of the present invention will be described below.

The case where the polymer constituting the continuous phase of the composite has a sulfate group cross-linkage and the case where it does not have a sulfate group cross-linkage will be described separately below.

<Polymer Having a Sulfate Group Cross-linkage>

Step (1)

A substrate with sulfur (S) bonded or adsorbed to the surface thereof is formed.

To form it, instead of using a piranha solution (also known as a piranha solution), an aqueous solution of persulfate and sulfuric acid can be employed. The use of sodium persulfate ($Na_2S_2O_8$) as the persulfate is desirable from the perspective of permitting the preparation of a catalyst or catalyst precursor with high activity. The concentration of sodium persulfate and the concentration of sulfuric acid in the aqueous solution of sodium persulfate and sulfuric acid can be suitably determined by taking into account the desired amount of sulfur (S) bonds and adsorption to the substrate surface, the number of sulfate group cross-linkages to be introduced into the polymer, and the like. For example, the substrate can be immersed for 1 to 30 minutes in the aqueous solution of persulfate and sulfuric acid, followed by washing and drying as needed to obtain a substrate on which sulfur (S) has been bonded or absorbed. However, substrate having a surface comprised of a material that the aqueous solution of persulfate and sulfuric acid tends not to react with is employed in this processing. Examples are gold and glass.

Step (2)

On the above mentioned surface of the substrate on which sulfur (S) has been bonded or adsorbed, in the presence of a catalytic metal compound, benzene compounds having two or more alkyl groups are dehydrogenatively condensed to form a composite. In the benzene compounds having two or more alkyl groups, when the alkyl groups have 1 to 3 carbon atoms and there are two alkyl groups, the alkyl groups are present at positions 1 and 4. It is also possible for the benzene compounds to have 3 or 4 alkyl groups. In that case, the alkyl groups are present at positions 1, 2, and 4 or at positions 1, 2, 4, and 5, respectively. The two or more alkyl groups are desirably identical, but can be different. Representative benzene compounds having two or more alkyl groups are paraxylene (paradimethylbenzene) and paradiethylbenzene. It is also possible to employ different types of benzene compounds in combination. The catalytic metal is as set forth above. The compound can be in the form of, for example, a salt or complex of a catalytic metal. Examples of catalytic metal compounds are inorganic salts such as hydrochlorides, sulfates, and nitrates; metal salts of organic acids such as acetates and lactates; and metal complexes such as phosphine complexes, acetylacetonate complexes or dibenzylideneacetone (dba), for example. The organic metal complexes are not necessarily limited to those having metal-carbon bonds, but can also be complexes containing organic substances in ligand moieties. Examples of desirable organic metal complexes are tetrakis triphenylphosphine palladium ($Pd(PPh_3)_4$) and dibenzylideneacetone palladium ($Pd(dba)_2$). However, no limitation to these compounds is intended.

The example of the case where the catalytic metal compound is palladium acetate ($Pd(OAc)_2$) and the benzene compound is p-xylene will be described. The above mentioned substrate is immersed with heating in a p-xylene solution of palladium acetate. The heating temperature is suitably determined by taking into account the boiling point of the benzene compound. In the case of p-xylene (boiling point 138° C.), heating is conducted at or below the boiling point at 80 to 138° C., for example. During heating, it is desirable to stir the solution from the perspective of facilitating dispersion of the catalytic metal compound. Heating can conducted for a period of 1 to 24 hours, for example. In the heating step, a polymer of p-xylene is produced on the surface of the substrate on which sulfur (S) has been bonded or adsorbed, and palladium nanoparticles derived from the palladium acetate are produced in the polymer in a dispersed state. Next, the substrate that has been obtained is, as desired, washed with p-xylene (desirably the same benzene compound as that employed above) and dried.

Next, the substrate that has been obtained is desirably heated to a temperature higher than the above heating temperature in a solution comprised of p-xylene (desirably the same benzene compound as that employed above). The heating temperature, as above, can be suitably determined by taking into account the boiling point of the benzene compound; in the case of p-xylene (boiling point 138° C.), heating can be conducted at or below the boiling point at 100 to 138° C., for example. Heating can be conducted for a period of 1 to 24 hours, for example. In the previous stage of heating, palladium nanoparticles are formed in a dispersed state in the polymer, but unreacted catalytic metal compound sometimes remains. Accordingly, this heat treatment contributes to eliminating unreacted catalytic metal compounds or converting them to nanoparticles. Following heating, as needed, washing with p-xylene (desirably the same benzene compound as that employed above) and drying can be conducted.

In this manner, a composite in which catalytic metal (palladium, for example) nanoparticles are dispersed is formed on the substrate surface in a self-assembling manner in a layered polymer.

<Polymer not Having a Sulfate Group Cross-linkage>

When manufacturing a polymer not having a sulfate group cross-linkage, step (2) above can be implemented on a substrate that has been prepared without implementing step (1). The surface of the substrate can be subjected to step (2) without any particular pretreatment, or, as desired, can be washed by the usual methods prior to being subjected to step (2) above. Since step (1) is not implemented in this method, a substrate comprised of a material capable of withstanding the heating treatment of step (2) can be employed.

The composite of the present invention that is formed on the surface of the substrate can have a thickness of 10 to 1,000 nm, for example. In practical terms, it can have a thickness ranging from 20 to 200 nm. The thickness of the composite can be suitably varied by selecting the processing conditions in step (2) above. The quantity of the catalytic metal nanoparticles contained in the polymer of the composite can also be suitably varied by selecting the processing conditions in step (2) above, such as the quantity of catalytic metal that is added during the heat treatment.

<The Catalyst or Catalyst Precursor>

The present invention includes a catalyst, or catalyst precursor, for a coupling reaction containing the composite or composite structure of the present invention set forth above. By way of example, the coupling reaction can be a reaction employing a halogenated hydrocarbon as at least part of the starting material or as an additive. The coupling reaction can be a carbon-carbon bond-forming reaction or a carbon-nitrogen bond-forming reaction.

<Reaction Employing Catalyst Precursor>

The catalyst precursor of the present invention does not exhibit catalytic activity by itself. For example, when immersed in a desired reaction solution, the catalytic metal nanoparticles supported by the polymer constituting the composite (catalyst precursor) are gradually released, and the catalytic metal nanoparticles that have been gradually released become a catalytically active species. For example, the method of use of the catalyst precursor according to the present invention consists of placing a halogenated hydrocarbon compound in a solution as a starting material or a portion of a starting material, and immersing the catalyst precursor according to the present invention in the solution to release a catalytically active species in the form of the nanoparticles from the catalyst precursor. Here, examples of the halogenated hydrocarbon compound will be described for the various reactions set forth farther below.

It suffices for the organic reaction employing the catalyst precursor of the present invention, such as a mesh-like catalyst precursor, to be a reaction in which catalytic metal nanoparticles supported on the mesh exhibit activity; there is no restriction to a specific reaction. There is no limitation to a reaction forming new bonds such as those given by way of example above; various reactions such as hydrogen reduction reactions, asymmetric synthesis reactions, and substitution reactions are included.

<The Method for Manufacturing a Coupling Product>

The present invention includes a method for manufacturing a coupling product comprising employing the composite or composite structure of the present invention set forth above to cause a plurality of organic compounds to undergo a coupling reaction yielding a coupling product. In the coupling reaction, it is desirable to employ a halogenated hydrocarbon as at least a part of the starting material or as an additive from the perspective of promoting the release of a catalytically active species in the form of the catalytic metal nanoparticles from the catalyst precursor and efficiently supplying them to the coupling reaction. The coupling reaction can be, for example, a carbon-carbon bond-forming reaction or a carbon-nitrogen bond-forming reaction. Specific examples of the coupling reaction are set forth farther below.

(Suzuki-Miyaura Coupling)

The present invention provides a method for manufacturing an organic compound by employing the catalyst precursor of the present invention set forth above, and bringing the metal catalyst precursor into contact with a reaction starting material in the form of an organic compound to result in the reaction generating new carbon-carbon bonds or carbon-hetero atom bonds. A desirable example of the method of manufacturing an organic compound employing the metal catalyst precursor of the present invention is a method for manufacturing a diaryl derivative, alkenylaryl derivative, or 1,3-diene by means of a condensation reaction of an aryl halide or an alkenyl halide and an aryl boron derivative or vinyl boron derivate. An example is the method of manufacturing a biphenyl derivative by condensing a halogenated benzene and phenylboronic acid.

Examples of the halogen in the aryl halide or alkenyl halide in the manufacturing method of the present invention are chlorine atoms, bromine atoms, and iodine atoms. Examples of the aryl group in the aryl halide are carbocyclic aromatic groups and heterocyclic aromatic groups. Examples of carbocyclic aromatic groups are monocyclic, polycyclic, and fused ring carbocyclic aromatic groups having 6 to 36 carbon atoms, desirably 6 to 18 carbon atoms, and preferably 6 to 12 carbon atoms. Examples of such carbocyclic aromatic groups are phenyl groups, naphthyl groups, biphenyl groups, phenanthryl groups, and anthryl groups. Examples of heterocyclic aromatic groups are monocyclic, polycyclic, and fused ring heterocyclic groups having rings with 3 to 8 members, desirably 5 to 8 members, comprising hetero atoms in the form of 1 to 4, desirably 1 to 3, or 1 or 2, nitrogen atoms, oxygen atoms, or sulfur atoms. Examples of such heterocyclic groups are furyl groups, thienyl groups, pyrrolyl groups, pyridyl groups, indole groups, and benzoimidazolyl groups. These aryl groups can comprise further substituents. So long as they do not negatively impact the reaction, such substituents are not specifically limited. Examples are the above halogen atoms, nitro groups, substituted or unsubstituted alkyl groups having 1 to 20, desirably 1 to 10, carbon atoms, substituted or unsubstituted alkoxy groups having 1 to 20, desirably 1 to 10 carbon atoms, and substituted or unsubstituted alkoxycarbonyl groups having 1 to 20, desirably 1 to 10, carbon atoms. Examples of the alkenyl group in the alkenyl halides are substituted or unsubstituted vinyl groups. Examples of substituents on the vinyl group are substituted or unsubstituted alkyl groups having 1 to 20, desirably 1 to 10, carbon atoms, substituted or unsubstituted alkenyl groups having 1 to 20, desirably 1 to 10, carbon atoms, substituted or unsubstituted aryl groups having 6 to 20, desirably 6 to 10, carbon atoms, and substituted or unsubstituted aralkyl groups having 7 to 20, desirably 7 to 12, carbon atoms. So long as they do not negatively affect the reaction, substituents on these groups are not specifically limited.

In the manufacturing method, examples of the boron derivative are mono, di, and triesters, and their derivatives, of orthoboric acid. However, there is not necessarily a limitation to orthoboric acid and its derivatives. Examples of the aryl group in the aryl boron derivative are substituted or unsubstituted phenyl groups, naphthyl groups, pyridine groups, furyl groups, and other aromatic rings. Substituents on these groups are not specifically limited so long as they do not negatively affect the reaction. Examples are halogen atoms such as chlorine atoms, bromine atoms, and iodine atoms, substituted or unsubstituted alkyl groups having 1 to 20, desirably 1 to 10, carbon atoms, and substituted or unsubstituted alkoxy groups having 1 to 20, desirably 1 to 10, carbon atoms. Examples of the vinyl group of the vinyl boron derivatives are substituted or unsubstituted vinyl groups. Substituents on these groups are not specifically limited so long as they do not negatively affect the reaction.

The manufacturing method of the present invention is desirably conducted in a polar solvent such as acetonitrile or ethanol. The reaction temperature can be selected within a range of from room temperature to the boiling point of the solvent.

Since the catalyst precursor of the present invention is a solid phase, once the reaction has ended, the usual processing methods such as removal, condensation, and extraction of the solid phase catalyst precursor can be used to separate the targeted product. Various purification methods can be used to purify and isolate the targeted product.

(Mizorogi-Heck Reaction)

An example of the method of manufacturing an organic compound employing the metal catalyst precursor of the present invention is the method of manufacturing an aryl alkene or 1,3-diene by the condensation reaction of an alkene and a halide having a carbon-carbon double bond or a sulfonate having a carbon-carbon double bond.

In this manufacturing method, examples of the alkene are ethylene derivatives having at least one hydrogen atom. Examples are ethylene derivatives in which at least one hydrogen atom of ethylene has been replaced with a keto group, substituted or unsubstituted akoxycarbonyl group, and/or a substituted or unsubstituted aryl group. Examples of the aryl group are the carbocyclic aromatic groups and heterocyclic aromatic groups set forth above. Substituents on these are not specifically limited so long as they do not negatively affect the reaction; examples are the above-mentioned substituents. Examples of preferred alkenes are substituted or unsubstituted 3-ketoalkenes, substituted or unsubstituted styrene derivatives, and substituted or unsubstituted (meth)acrylic esters. Examples of the ester residue of the acrylic ester is a substituted or unsubstituted alkyl group having 1 to 20, desirably 1 to 10, carbon atoms. Substituents on these are not specifically limited so long as they do not negatively affect the reaction. Examples of desirable alkenes are acrylic esters such as methyl acrylate, 3-ketoalkenes such as 3-ketobutene, and styrene derivatives such as styrene. However, these compounds are not intended as limitations.

Examples of the halogen in the halide having a carbon-carbon double bond are chlorine, bromine, and iodine atoms. Examples of sulfonates having carbon-carbon double bonds are sulfonic acid and its derivatives, such as various metal salts such as sodium salts and potassium salts of sulfonic acid, and an ammonium salt. It suffices for the group having the carbon-carbon double bond to be a group having an aliphatic carbon-carbon double bond or an aromatic carbon-carbon double bond. Examples are substituted or unsubstituted vinyl groups and substituted or unsubstituted aryl groups. Examples of aryl groups are the carbocyclic aromatic groups and heterocyclic aromatic groups set forth above. Substituents on these compounds are not specifically limited so long as they do not negatively affect the reaction.

This manufacturing method is desirably conducted in a polar solvent such as acetonitrile or ethanol. The reaction temperature can be selected within a range of from room temperature to the boiling point of the solvent.

Because the catalyst precursor of the present invention is a solid phase, once the reaction has ended, the usual processing methods such as removal, condensation, and extraction of the solid phase catalyst precursor can be used to separate the targeted product. Various purification methods can be used to purify and isolate the targeted product.

(Stille Coupling)

An example of the method of manufacturing an organic compound employing the metal catalyst precursor of the present invention is the method of manufacturing a biaryl, aryl alkene, or 1,3-diene by the condensation reaction of a tin compound having a carbon-carbon double bond and an aryl halide or alkenyl halide.

In this manufacturing method, an example of a substituent on the tin compound is an aryl group, such as an aromatic ring such as a substituted or unsubstituted phenyl group, naphthyl group, pyridine group, or furyl group. Substituents on these compounds are not specifically limited so long as they do not negatively affect the reaction. Examples are halogen atoms such as chlorine, bromine, and iodine atoms, substituted or unsubstituted alkyl groups having 1 to 20, desirably 1 to 10, carbon atoms, and substituted or unsubstituted alkoxy groups having 1 to 20, desirably 1 to 10, carbon atoms. Tin compounds comprising vinyl groups are also included: examples of the vinyl group are substituted or unsubstituted vinyl groups. Substituents on these compounds are not specifically limited so long as they do not negatively affect the reaction.

This manufacturing method is desirably conducted in a polar solvent such as acetonitrile or ethanol. The reaction temperature can be suitably selected within a range of from room temperature to the boiling point of the solvent.

Because the catalyst precursor of the present invention is a solid phase, once the reaction has ended, the usual processing methods such as removal, condensation, and extraction of the solid phase catalyst precursor can be used to separate the targeted product. Various purification methods can be used to purify and isolate the targeted product.

(Sonogashira Coupling)

An example of the method for manufacturing an organic compound employing the metal catalyst precursor of the present invention is a manufacturing method that provides an aryl alkyne or alkynyl alkyne by the condensation reaction of an alkyne and a halide having a carbon-carbon double bond.

In this manufacturing method, examples of substituents on the alkyne are substituted or unsubstituted aromatic groups such as phenyl groups, naphthyl groups, pyridyl groups, and furyl groups. Substituents on these groups are not specifically limited so long as they do not negatively affect the reaction. Examples are halogen atoms such as chlorine, bromine, and iodine atoms; substituted or unsubstituted alkyl groups having 1 to 20, desirably 1 to 10, carbon atoms; and substituted or unsubstituted alkoxy groups having 1 to 20, desirably 1 to 10, carbon atoms. Examples of substituents on the alkyne group are substituted or unsubstituted vinyl groups. Substituents on these groups are not specifically limited so long as they do not negatively affect the reaction.

Examples of the halogen in the halide having a carbon-carbon double bond in the present manufacturing method are chlorine, bromine, and iodine atoms. Examples of the sulfonate having a carbon-carbon double bond are sulfonic acid or its derivatives. Examples are ammonium salts and various metal salts, such as sodium salts and potassium salts, of sulfonic acid. It suffices for the group having a carbon-carbon double bond to be a group having an aliphatic carbon-carbon double bond or an aromatic carbon-carbon double bond. Examples are substituted or unsubstituted vinyl groups and substituted or unsubstituted aryl group. Examples of the aryl group are the above carbocyclic aromatic groups and heterocyclic aromatic groups. Substituents on these groups are not specifically limited so long as they do not negatively affect the reaction.

This manufacturing method is desirably conducted in a polar solvent such as acetonitrile or ethanol. The reaction temperature can be suitably selected within a range of from room temperature to the boiling point of the solvent.

Because the catalyst precursor of the present invention is a solid phase, once the reaction has ended, the usual processing methods such as removal, condensation, and extraction of the solid phase catalyst precursor can be used to separate the targeted product. Various purification methods can be used to purify and isolate the targeted product.

(Buchwald-Hartwig Coupling)

Examples of the method of manufacturing an organic compound employing the metal catalyst precursor of the present invention are manufacturing methods that employ reactions that form carbon-hetero atom bonds. A desirable example is a reaction that forms a carbon-oxygen or carbon-sulfur, and preferably, a carbon-nitrogen bond. An example is a method of manufacturing a substituted amine by subjecting an amine having one or more alkyl groups or aryl groups and a halide having a carbon-carbon double bond to a condensation reaction.

In this manufacturing method, examples of the substituents on the amine are substituted or unsubstituted alkyl groups having 1 to 20, desirably 1 to 10, carbon atoms; aromatic groups such as substituted or unsubstituted phenyl groups, naphthyl groups, pyridyl groups, and furyl groups. Substituents on these groups are not specifically limited so long as they do not negatively affect the reaction. Examples are halogen atoms such as chlorine, bromine, and iodine atoms; substituted or unsubstituted alkyl groups having 1 to 20, desirably 1 to 10, carbon atoms; and substituted or unsubstituted alkoxy groups having 1 to 20, desirably 1 to 10, carbon atoms.

In this manufacturing method, examples of the halogen in the halide having a carbon-carbon double bond are chlorine, bromine, and iodine atoms. Examples of the sulfonate having a carbon-carbon double bond are sulfonic acid and its derivatives. Examples are ammonium salts and various metal salts of sulfonic acid, such as sodium salts and potassium salts. It suffices for the group having a carbon-carbon double bond to be a group having an aliphatic carbon-carbon double bond or an aromatic carbon-carbon double bond, such as a substituted or unsubstituted vinyl group or substituted or unsubstituted aryl group. Examples of the aryl group are the carbocyclic aromatic groups and heterocyclic aromatic groups given above. Substituents on these groups are not specifically limited so long as they do not negatively affect the reaction.

This manufacturing method is desirably conducted in a polar solvent such as acetonitrile or ethanol. The reaction temperature can be suitably selected within a range of from room temperature to the boiling point of the solvent.

Because the catalyst precursor of the present invention is a solid phase, once the reaction has ended, the usual processing methods such as removal, condensation, and extraction of the solid phase catalyst precursor can be used to separate the targeted product. Various purification methods can be used to purify and isolate the targeted product.

EXAMPLES

The present invention will be described in greater detail through examples below. However, there is no intent to limit the present invention to these examples.

Example 1

<Example Employing P-xylene (Pd)>
Method of Fabricating "Self-assembled Multilayered Palladium Nanoparticles by Adsorbing a Palladium Complex on a Metal Substrate"

A mesh-like gold substrate (12×14 mm, 100 mesh) was immersed for 5 minutes in a piranha solution prepared from concentrated sulfuric acid (4.7 g), $Na_2S_2O_8$ (4.0 g), water (4 g) and ice (13 g). It was then washed with water and ethanol, and dried under reduced pressure, yielding a gold substrate to which sulfur (S) had been bonded or adsorbed. The gold substrate to which sulfur (S) had been bonded or adsorbed that was obtained was stirred for 12 hours at 100° C. in a p-xylene solution (3.0 mL) of palladium acetate ($Pd(OAc)_2$) (5.3 mg). The substrate obtained was washed with a washing solution comprised of p-xylene and dried at room temperature under 6 mmHg reduced pressure. The substrate obtained was heated for 12 hours at 135° C. in a solution comprised of p-xylene, and then thoroughly washed with a solution comprised of p-xylene. Subsequently, it was vacuum dried for 10 minutes at room temperature at 6 mmHg reduced pressure, yielding the composite with substrate of the present invention (PdNSXP (Nanoparticle Sulfated Xylene Polymer)).

Figure 2:
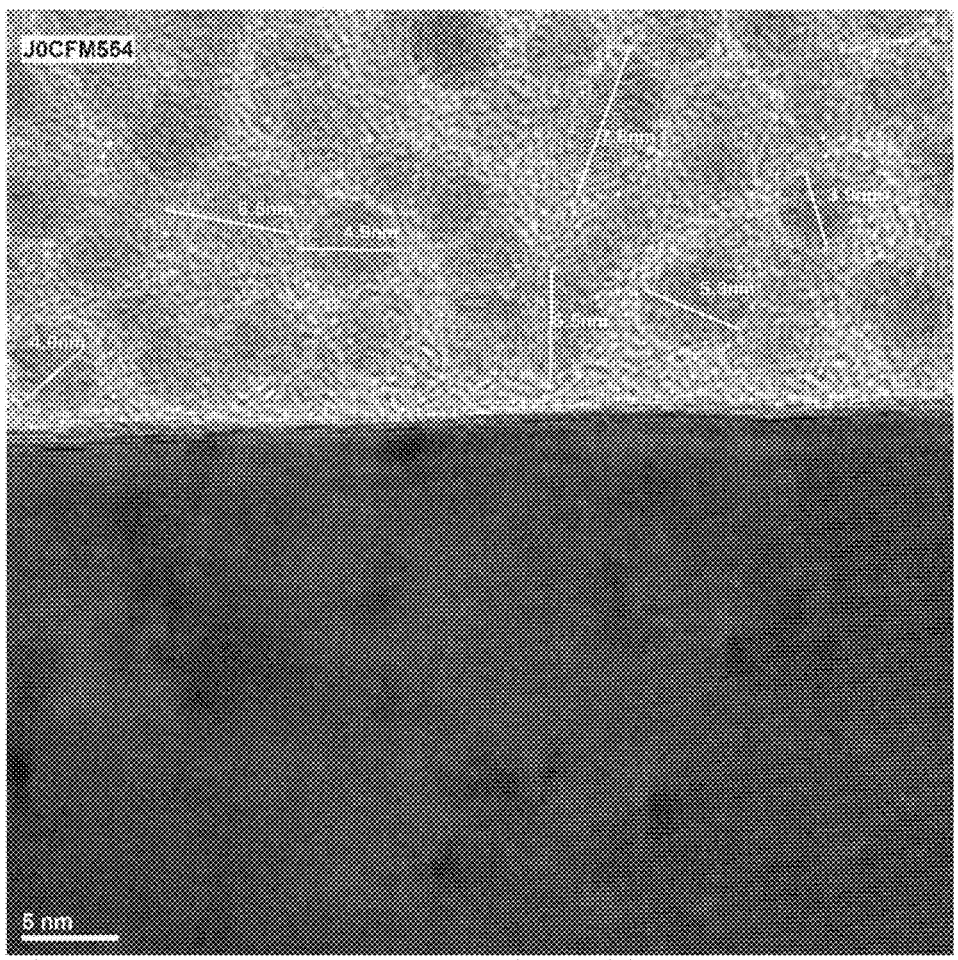
FIG. 2 A cross-sectional TEM image of the composite with substrate of the present invention obtained in Example 1.
Figure 3:
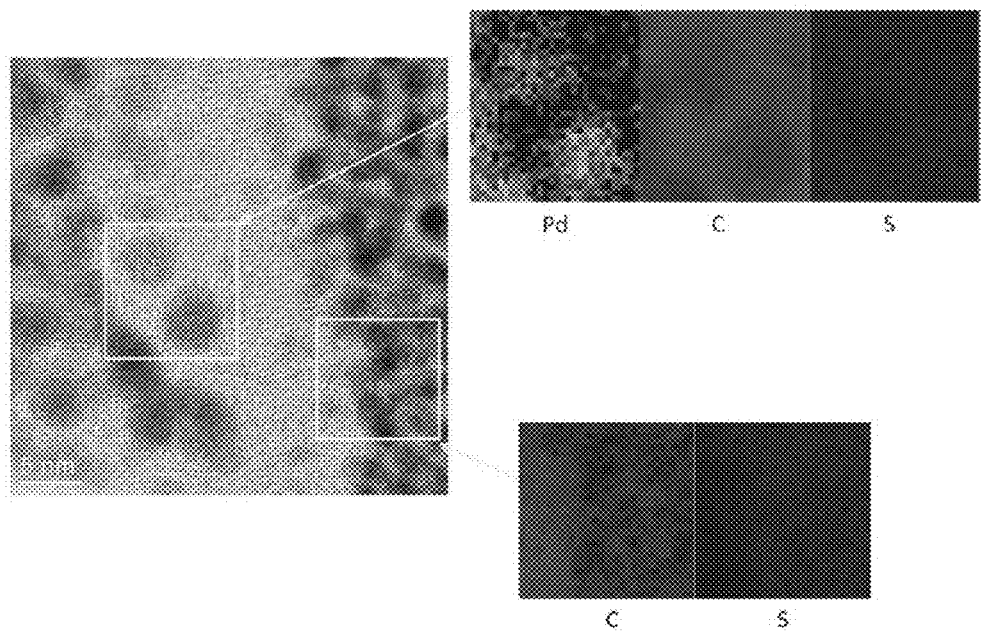
FIG. 3 A cross-sectional SEM-EELS image of the composite with substrate of the present invention obtained in Example 1.

FIGS. 1 and 2 show cross-sectional TEM images of the composite with substrate of the present invention obtained above. FIG. 3 shows a cross-sectional SEM-EELS image. Based on these results, it was revealed that palladium nanoparticles (PdN) with a longer axis ranging from 3 to 8 nm were dispersed in a carbon layer and sulfur accompanying to the palladium nanoparticles was present.

Figure 4:
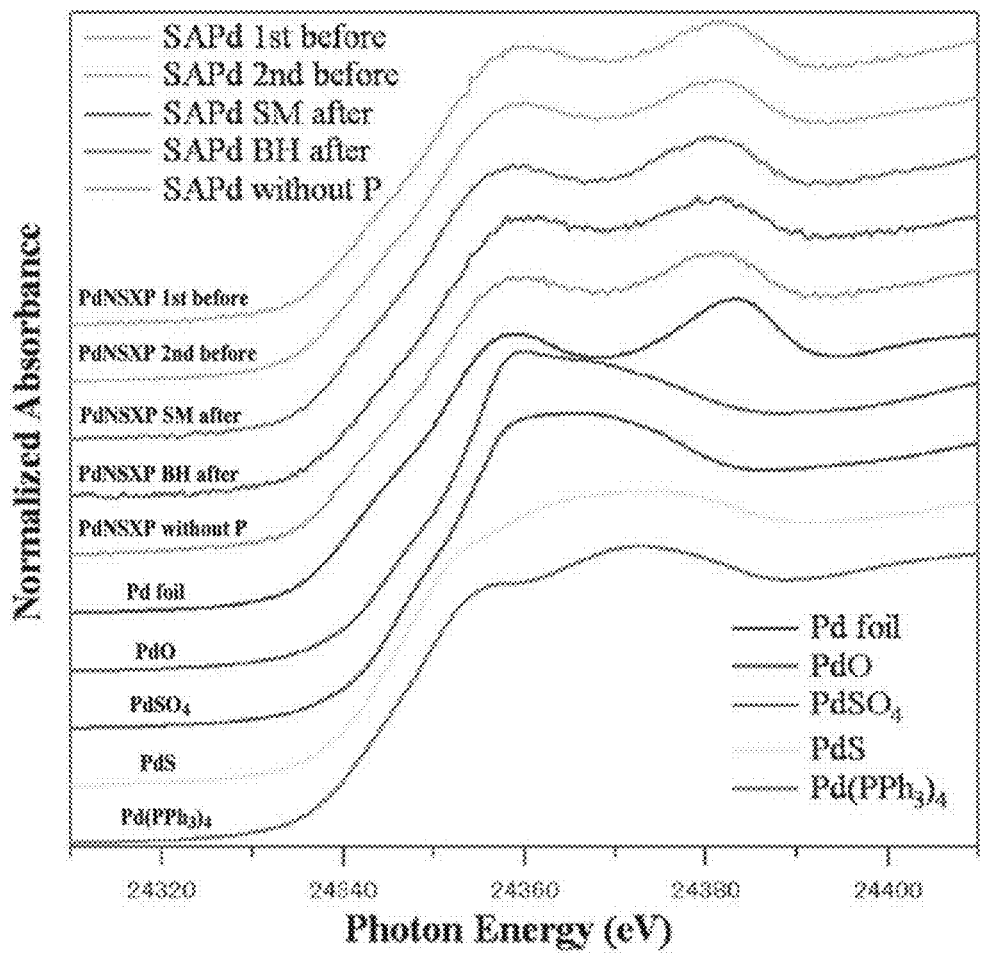
FIG. 4 An X-ray absorption fine structure (XAFS Pd—K) spectrum of the composite with substrate of the present invention obtained in Example 1 after being repeatedly used 10 times in the reactions of Examples 2-1 and 2-2.

FIG. 4 shows the X-ray absorption fine structure (XAFS Pd—K) spectrum of the composite with substrate (denoted as PdNSXP in the figure) of the present invention obtained above. In FIG. 4, the results for Pd foil, PdO, $PdSO_4$, PdS, and $Pd(PPH_3)_4$ are also given for reference. The fact that the shape of the spectrum of the Pd in the composite resembles that of Pd foil suggests metallic Pd.

Figure 5:
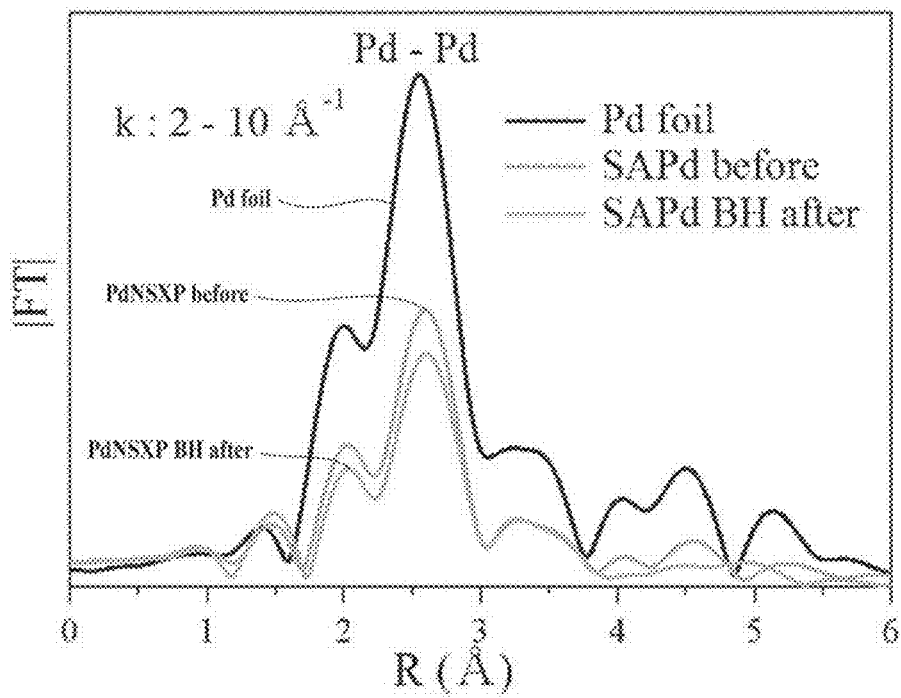
FIG. 5 An X-ray absorption fine structure (Pd—K edge extended XAFS) spectrum of the composite with substrate of the present invention obtained in Example 1 following use in the reaction of Example 2-2.

FIG. 5 shows an X-ray absorption fine structure (Pd—K edge extended XAFS) spectrum of the composite with substrate (denoted as PdNSXP before in the figure) of the present invention obtained above. In FIG. 5, the spectrum of Pd foil is also shown for reference. Based on these results, the shape of the spectrum is similar to that of Pd foil, indicating that the Pd in the composite was metallic Pd and had a particle diameter of 3 nm.

Figure 6:
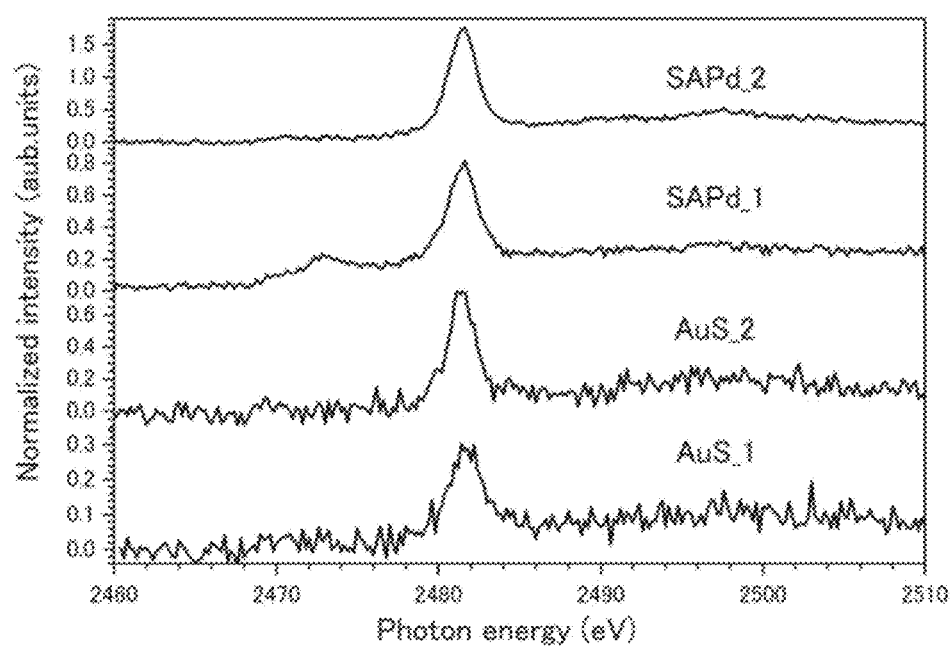
FIG. 6 An X-ray absorption fine structure (XAFS Pd—K) spectrum of the composite with substrate of the invention obtained in Example 1.
Figure 7:
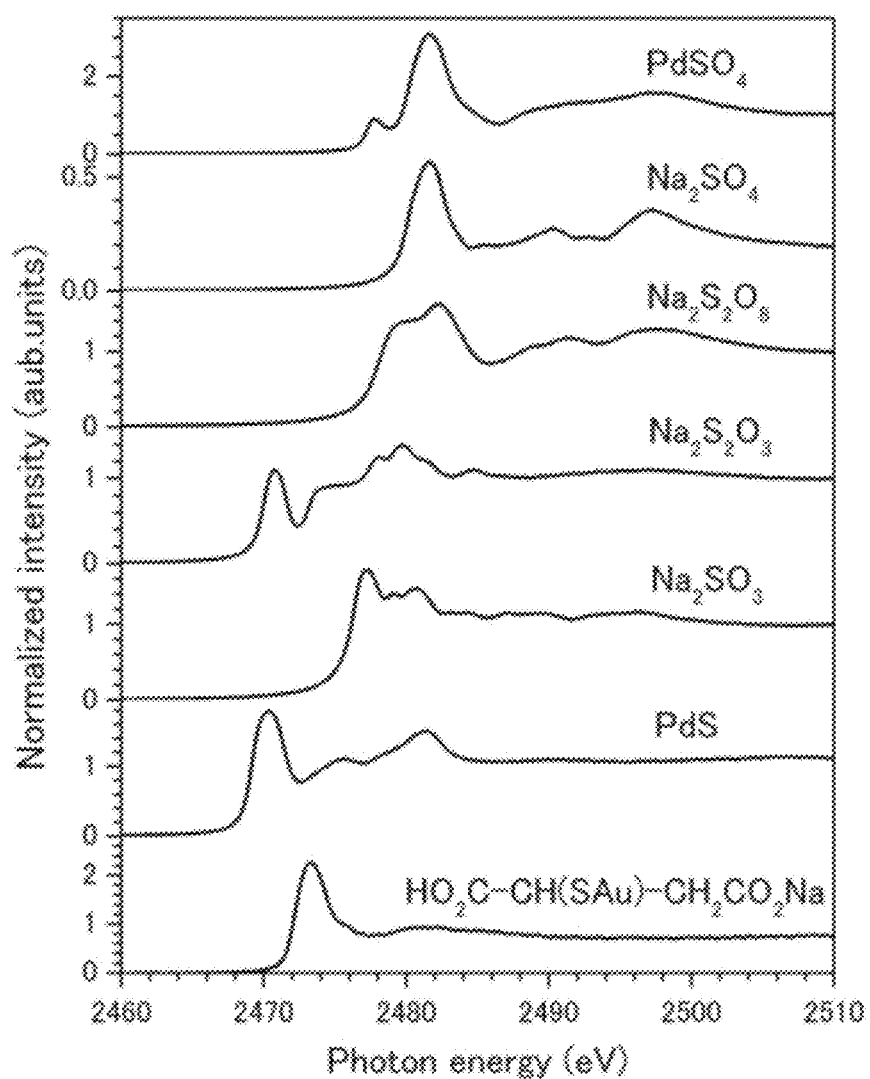
FIG. 7 X-ray absorption fine structure (XAFS Pd—K) spectra of various compounds containing sulfur for reference.

FIG. 6 shows the X-ray absorption fine structure (XAFS Pd—K) spectrum of the composite with substrate (denoted as PdNSXP in the figure) of the present invention obtained above. In FIG. 7, the results of X-ray absorption fine structure (XAFS Pd—K) of various compounds containing sulfur are given for reference.

Figure 8:
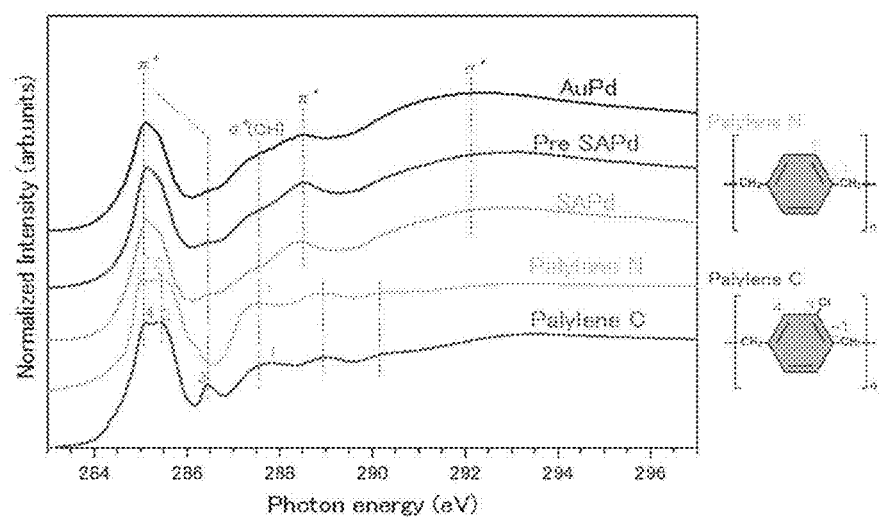
FIG. 8 An X-ray absorption fine structure (XAFS C—K) spectrum of the compound with substrate of the present invention obtained in Example 1. AuPd, PalyleneN, and PalyleneC spectra are also provided for reference.

FIG. 8 gives the results of X-ray absorption fine structure (XAFS C—K) of the composite with substrate (PdNSXP) of the present invention obtained above. For reference, the results for AuPd, Palylene N, and Palylene C are also given. Based on these results, it was found that the composite of the present invention contained a polymer having a structure similar to that of Palylene N, and that the sulfur in the composite was present in the form of sulfate groups.

Example 2-1

<Suzuki-Miyaura Coupling Employing Catalyst Precursor>
The mesh-like composite with substrate (PdNSXP=catalyst precursor) (12×14 mm) of the present invention obtained in Example 1 was added to an ethanol solution (3 mL) of iodobenzene (102 mg), 4-chlorophenyl boronate (117 mg), and potassium carbonate (138 mg) and heated at 80° C. for 12 hours. The reaction solution was then cooled to room temperature, and the catalyst precursor was washed with ethanol and removed from the reaction solution. The solvent was distilled off of the reaction solution under reduced pressure, after which the residue was purified by silica gel column chromatography (n-hexane) to quantitatively obtain the targeted 4-chlorobiphenyl. The catalyst precursor that had been removed was similarly reacted a second time, which also quantitatively yielded 4-chlorobiphenyl. More than a hundred times of this repeat were possible.

FIG. 4 shows the X-ray absorption fine structure (XAFS Pd—K) spectrum of the catalyst precursor following use in the above reaction 10 times. This is denoted as PdNSXP SM after in FIG. 7. FIG. 7 also shows the XAFS Pd—K of the catalyst precursor before the reaction. Based on the results of FIG. 7, the shape of the spectrum of the Pd in the catalyst precursor after being used 10 times in the above reaction was unchanged from the shape of the spectrum of the Pd of the catalyst precursor before the reaction, suggesting that Pd nanoparticles were contained.

Example 2-2

<Buchwald-Hartwig Reaction Employing Catalyst Precursor>

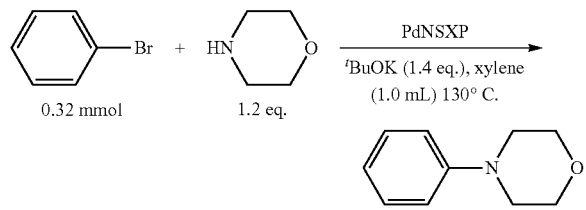

The catalyst precursor prepared in Example 1 was placed in a xylene solution (1.0 mL) containing bromobenzene (0.32 mmol), morpholine (1.2 equivalents), and tert-butoxypotassium (1.4 equivalents) and heated for 7 hours at 130° C. Subsequently, the reaction solution was cooled to room temperature. The catalyst precursor was washed with ethanol and removed from the reaction solution. The solvent was distilled off of the reaction solution under reduced pressure, after which the residue was purified by silica gel column chromatography (n-hexane:ethyl acetate=9:1), yielding 4-phenyl-morpholine. The catalyst precursor that had been removed was similarly reacted, and the targeted 4-phenyl-morpholine was obtained from the second through the tenth times. The average yield the tenth time around was 92%. The quantity of Pd supported after the tenth reaction was 68±18 µg.

Reaction liquid from each reaction cycle was subjected to ICP-MS and the quantity of Pd that elute into the solution was measured. The results are given in Table 1.

TABLE 1

| Cycle | 1st | 2nd | 3rd | 4th | 5th | 6th | 7th | 8th | 9th | 10th |
|---|---|---|---|---|---|---|---|---|---|---|
| Amount of Pd that eluted (ng) | 588 ± 494 | 359 ± 204 | 61 ± 25 | 231 ± 64 | 202 ± 51 | 419 ± 152 | 294 ± 94 | 205 ± 47 | 339 ± 85 | 320 ± 65 |
| Amount of Pd that eluted (ppm) | 0.6 | 0.4 | 0.06 | 0.2 | 0.2 | 0.4 | 0.3 | 0.2 | 0.3 | 0.3 |

FIG. 4 shows an X-ray absorption fine structure (XAFS Pd—K) spectrum of the catalyst precursor after 10 cycles of use in the above Buchwald-Hartwig reaction, denoted as PdNSXP BH after. An XAFS Pd—K spectrum of the catalyst precursor before the reaction is also shown in FIG. 4. Based on the results of FIG. 4, the shape of the spectrum of the Pd in the catalyst precursor after 10 cycles of use in the above reaction was unchanged from the shape of the spectrum of the Pd in the catalyst precursor before the reaction, suggesting that Pd nanoparticles were contained.

Example 2-3

<Buchwald-Hartwig Reaction Employing Catalyst Precursor>

Figure 9:
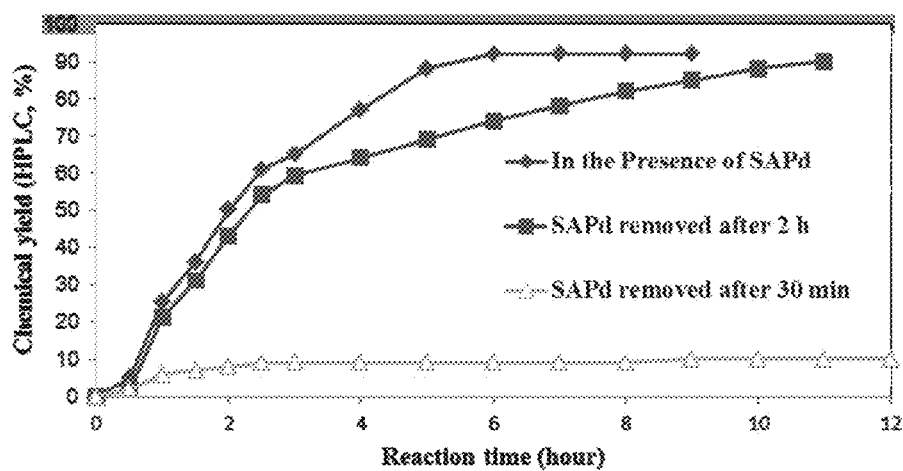
FIG. 9 Shows the change over time in the reaction yield in Example 2-3.

Under the same conditions as in Example 2-2, except that the catalyst precursor prepared in Example 1 was placed in a mixed liquid of reaction-use starting materials, the catalyst precursor was removed after 30 minutes at 130° C. (Conditions A), the catalyst precursor was heated to 130° C., and the reaction yield was measured. (Conditions B) were identical to Conditions A with the exception that the catalyst precursor was removed after two hours. (Conditions C) were identical to Conditions A with the exception that the catalyst precursor was not removed. The change over time in the reaction yield is shown in FIG. 9. Based on the results in FIG. 9 and the results in Table 2 below, a certain amount of time was found to be required for a specified quantity of Pd nanoparticles to elute into the reaction solution. In this system, it was found that the quantity of Pd nanoparticles required by the reaction had not eluted into the reaction solution at 30 minutes, but that the quantity of Pd nanoparticles required by the reaction had eluted at 2 hours.

Table 2 shows the amount of Pd (ng) that eluted into the reaction solution at 30 minutes, 2 hours, and 7 hours after the start of the reaction.

TABLE 2

| Reaction time (eluting period) (hours) | Quantity of Pd that eluted (ng) |
|---|---|
| 0.5 | 30 ± 0 |
| 2 | 205 ± 148 |
| 7 | 2920 ± 1952 |

Example 3

<Example Employing Ni>

Figure 10:
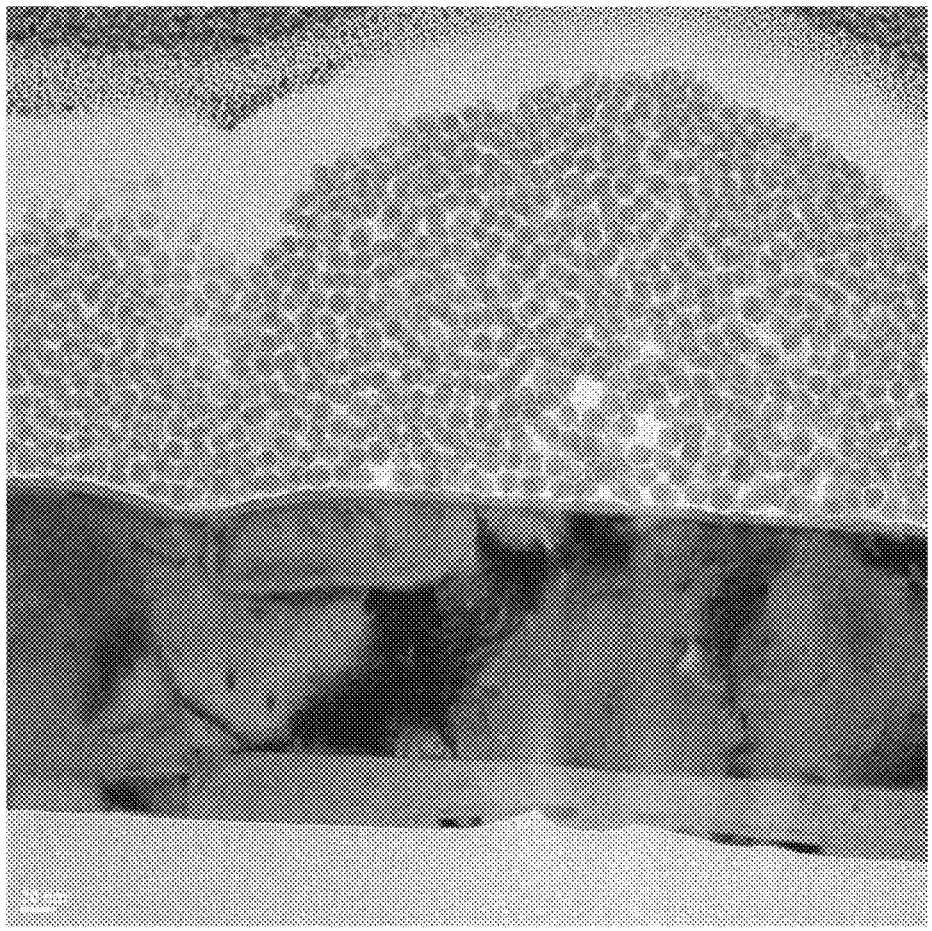
FIG. 10 A cross-sectional TEM image of the composite (NiNSXP) with substrate of the present invention prepared in Example 4.

The gold substrate on which sulfur (S) had been bonded or adsorbed that was obtained in Example 1 was placed in a diethylbenzene solution (2 to 3 mL) of Ni(acac)$_2$ (5.9 to 11.8 mg) and trioctylphosphine (200 to 70 µL) and stirring was conducted for 12 hours at 190 to 200° C. Subsequently, the substrate obtained was washed with p-xylene, dried under reduced pressure, placed in p-xylene (3 mL), and heated for 12 hours at 135° C. Subsequently, it was washed with p-xylene and then dried under reduced pressure to obtain the composite with substrate (NiNSXP) of the present invention. FIG. 10 shows a cross-sectional TEM image of the composite with substrate of the present invention above obtained. Based on the results, Ni nanoparticles (NiN) about 15 nm in diameter were found to be dispersed in a carbon layer. The fact that there was little variation in the diameter of the Ni nanoparticles was characteristic.

Example 4

<Suzuki-Miyaura Coupling Employing Catalyst Precursor with Ni Present on Substrate Surface>

The composite with substrate (NiNSXP=catalyst precursor) of the present invention prepared in Example 3 was added to a 1,4-dioxane (1 mL) of 4-bromoacetophenone (49.8 mg), phenylboronic acid (45.7 mg), and potassium carbonate (69 mg) and the mixture was heated to 100° C. for 12 hours. Subsequently, the reaction solution was cooled to room temperature, and the catalyst precursor was washed with ethanol and removed from the reaction solution. The solvent was distilled off of the reaction solution under reduced pressure, after which a portion of the reaction mixture was analyzed by NMR, yielding the targeted 4-acetylbisphenyl at 33%. The removed catalyst precursor that had been removed was similarly reacted, permitting recycling 10 times at 13 to 33% yields.

Example 5

<Example Employing Glass Instead of Gold>
Method of Fabricating a "Metal Catalyst Precursor in which a Palladium Complex was Adsorbed on a Glass Substrate"

A glass plate (10×11 mm) was immersed for 5 minutes in piranha solution prepared from concentrated sulfuric acid (4.7 g), $Na_2S_2O_8$ (4.0 g), water (4.0 g), and ice (13 g); washed with water and ethanol; and dried under reduced pressure, yielding a glass substrate on which sulfur (S) had been bonded or adsorbed. The glass substrate on which sulfur (S) had been bonded or adsorbed that was obtained was stirred for 12 hours at 100° C. in a p-xylene solution (3.0 mL) of palladium acetate (Pd(OAc)) (5.3 mg), causing the palladium (Pd) to bonded or adsorbed. Subsequently, the substrate that had been obtained was washed with a washing solution comprised of p-xylene and dried at room temperature under 6 mmHg reduced pressure to obtain a coarse metal catalyst in which Pd was bonded or adsorbed to a glass plate on which sulfur (S) had been bonded or adsorbed. The coarse metal catalyst obtained was heated for 12 hours at 135° C. in a solution comprised of p-xylene and then thoroughly washed with a solution comprised of p-xylene. Subsequently, it was vacuum dried for 10 minutes at room temperature under 6 mmHg reduced pressure, yielding the composite with substrate (PdNSXP) of the present invention.

Example 6

<Suzuki-Miyaura Coupling Employing Catalyst Precursor Using Glass Plate>

The composite with glass substrate (self-assembled multilayered palladium nanoparticles) (10×11 mm) of the present invention prepared in Example 5 was charged to an ethanol solution (3 mL) of bromobenzene (77.1 mg), 4-chlorophenylboronate (117 mg), and potassium carbonate (138 mg) and the mixture was heated at 80° C. for 12 hours. The reaction solution was then cooled to room temperature. A portion of the reaction solution was collected and HPLC was used to calculate the yield, revealing that the targeted 4-chlorobiphenyl had been produced at a yield of 89%. The PdNSXP employing glass that had been removed was similarly reacted, permitting recycling 10 times with yields of greater than or equal to 80%.

Example 7

<Example (Pd) not Employing Piranha Treatment>
Method of Fabricating "Self-assembled Multilayered Palladium Nanoparticles in which Palladium Complex was Adsorbed to Gold Substrate"

A gold substrate (12×14 mm, 100 mesh) was stirred for 12 hours at 100° C. in a p-xylene solution (3.0 mL) of palladium acetate (Pd(OAc)$_2$) (5.3 mg) to cause the palladium (Pd) to bond or adsorb. Subsequently, the substrate obtained was washed with a washing solution of p-xylene and dried at room temperature under 6 mmHg reduced pressure. The product obtained was then heated for 12 hours at 135° C. in a solution comprised of p-xylene and thoroughly washed with a solution comprised of p-xylene. Subsequently, it was vacuum dried for 10 minutes at room temperature under 6 mmHg reduced pressure, yielding the composite with substrate (PdNSXP) of the present invention.

Example 8

<Suzuki-Miyaura Coupling Employing Catalyst Precursor not Treated with Piranha Solution>

The composite with substrate (PdNSXP=catalyst precursor) (12×14 mm) of the present invention that had been prepared in Example 7 was added to an ethanol solution (3 mL) of iodobenzene (102 mg), 4-chlorophenyl boronate (117 mg), and potassium carbonate (138 mg) and heated at 80° C. for 12 hours. The reaction solution was then cooled to room temperature. The catalyst precursor was washed with ethanol and removed from the reaction solution. The solvent was distilled off of the reaction solution under reduced pressure and the residue was purified by silica gel column chromatography (n-hexane) to obtain the targeted 4-chlorobiphenyl at 90% yield. The mesh-like catalyst precursor that had been removed was similarly reacted. Yields of 87% and 81% were achieved in the second and third reaction cycles, respectively.

Example 9

<Example Employing Ru>
A mesh-like gold substrate (12×14 mm, 100 mesh) was immersed for 5 minutes in a piranha solution prepared from concentrated sulfuric acid (4.71 g), $Na_2S_2O_8$ (4.01 g), and ice (16.9 g); washed with water and ethanol; and dried under reduced pressure, yielding a gold substrate to which sulfur (S) had bonded or adsorbed. The gold substrate to which sulfur (S) had bonded or adsorbed that was obtained was stirred for 12 hours at 135° C. in a p-xylene solution (3 mL) of ruthenium acetate ($[Ru_3O(OAc)_6(H_2O)_3]OAc$) (6.7 mg). The substrate obtained was thoroughly washed in a solution comprised of p-xylene. Subsequently, drying was conducted under reduced pressure for 30 minutes, yielding the composite with substrate (RuNSXP) of the present invention.

Figure 11:
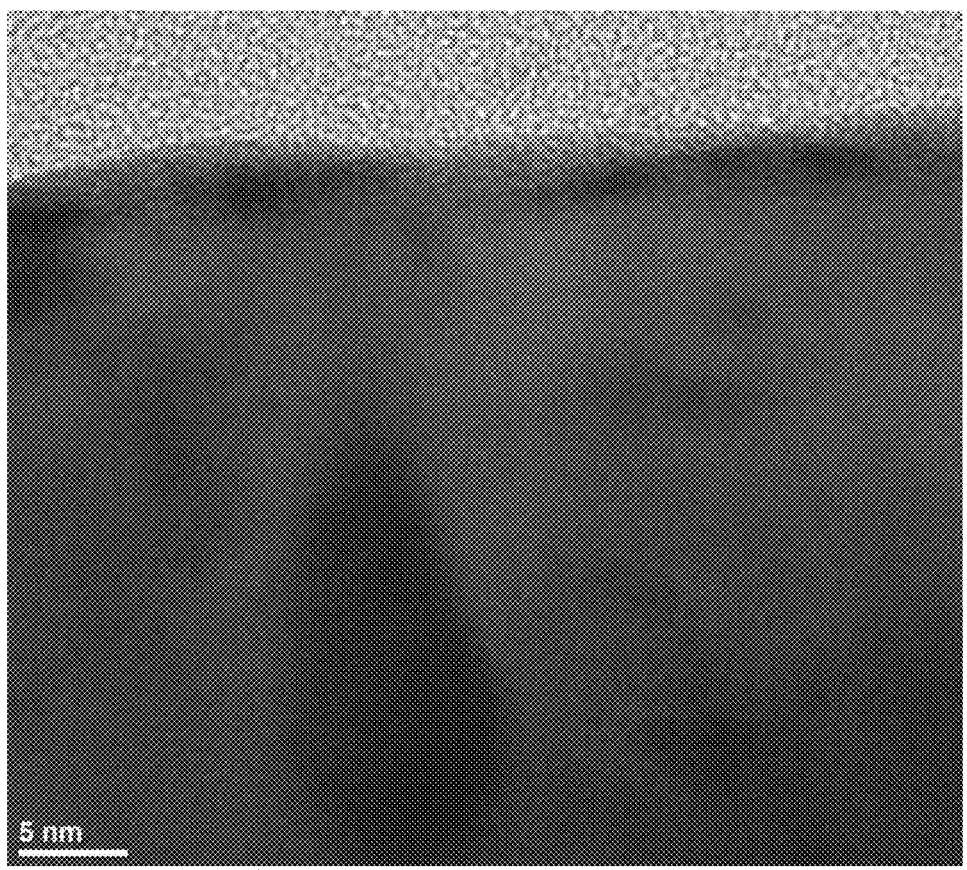
FIG. 11 A cross-sectional TEM image of the composite (RuNSXP) with substrate of the present invention prepared in Example 9.

FIG. 11 shows a cross-sectional TEM image of the composite with substrate of the present invention obtained above. Based on these results, it was found that ruthenium nanoparticles (RuN) with a longer axis ranging from 3 to 5 nm had been dispersed in a carbon layer, and the sulfur was present accompanying to the ruthenium nanoparticles.

Example 10

<Suzuki-Miyaura Coupling Employing Catalyst Precursor>
The composite with substrate (RuNSXP=catalyst precursor) (12×14 mm) of the present invention that had been prepared in Example 9 was added to a 1,2-dimethoxyethane solution (1 mL) of 4-iodoanisole (82.0 mg), phenylboronic acid (61.1 mg), and sodium hydroxide (29.2 mg) and heated at 105° C. for 8 hours. The reaction solution was then cooled to room temperature. The catalyst precursor was removed from the reaction solution. Water (1 mL) was added to the reaction solution and the mixture was heated at 120° C. for 24 hours. The residue was purified by silica gel column chromatography (n-hexane) to obtain 57 mg of the targeted 4-methoxybiphenyl (87.9% yield).

Example 11

<Repeated Reaction Test>

The catalyst precursor that was removed in Example 10 was added to a 1,2-dimethoxyethane (1 mL) solution of 4-iodoanisole and the mixture was heated at 60° C. for 3 hours. Subsequently, the reaction solution was cooled to room temperature and the catalyst precursor was removed from the reaction solution. An aqueous solution of phenylboronic acid (61.1 mg) and sodium hydroxide (29.2 mg) was added to the reaction solution and the mixture was heated at 120° C. for 24 hours. The residue was purified by silica gel column chromatography (n-hexane) to obtain 44.5 mg (68.8% yield) of the targeted 4-methoxybiphenyl.

Example 12

<Example Employing Au>

Figure 12:
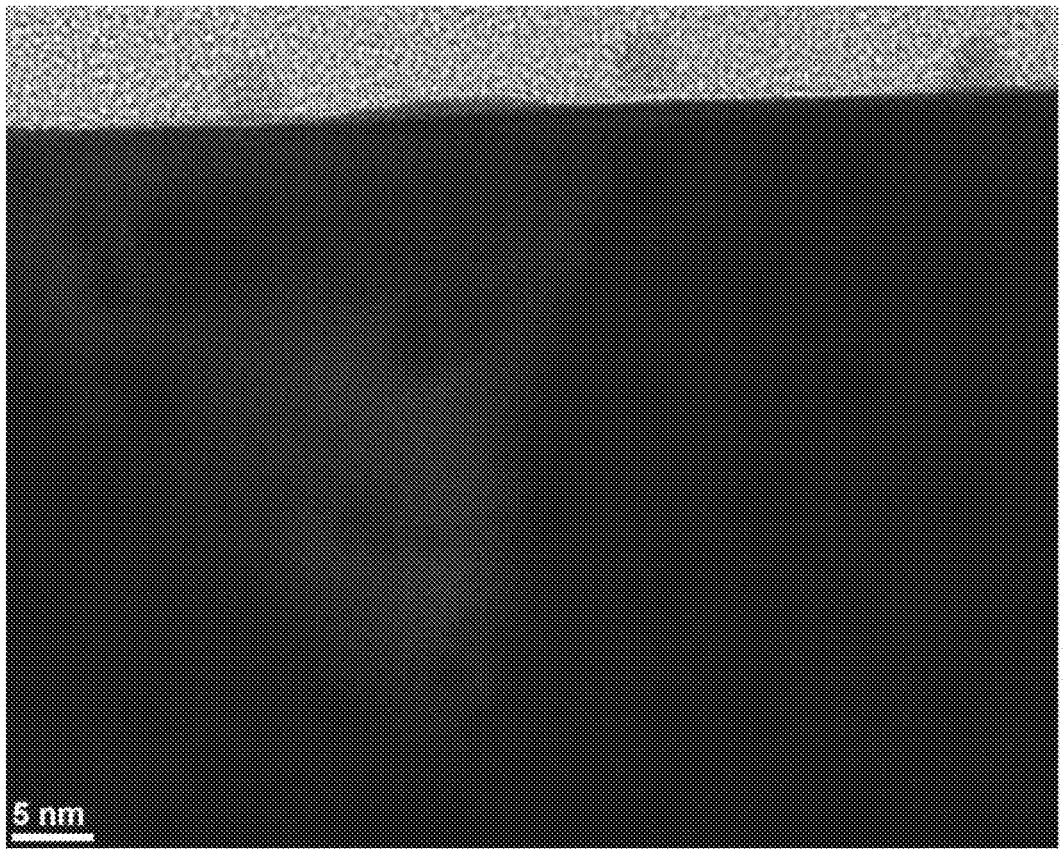
FIG. 12 A cross-sectional TEM image of the composite (AuNSXP) with substrate of the present invention prepared in Example 12.

A mesh-like gold substrate (12×14 mm, 100 mesh) was immersed for 5 minutes in piranha solution prepared from concentrated sulfuric acid (4.71 g), $Na_2S_2O_8$ (4.01 g), and ice (16.9 g); washed with water and ethanol; and dried under reduced pressure, yielding a gold substrate to which sulfur (S) had bonded or adsorbed. The gold substrate to which sulfur (S) had bonded or adsorbed that was obtained was stirred for 12 hours at 100° C. in a mixed chloroform and p-xylene solution (3 mL, chloroform:p-xylene (volumetric ratio=1:2)) of gold acetate $(Au(OAc)_3)$ (8.8 mg). The substrate obtained was thoroughly washed with a solution comprised of p-xylene. Subsequently, the substrate was dried for 30 minutes under reduced pressure, yielding the composite with substrate (AuNSXP) of the present invention. FIG. 12 shows a cross-sectional TEM image of the composite with substrate of the present invention obtained above. Based on these results, gold nanoparticles (AuN) with a longer axis ranging from 3 to 5 nm were found to have been dispersed in a carbon layer and sulfur was found to be present accompanying to the gold nanoparticles.

Example 13

<Example Employing Pt>

Figure 13:
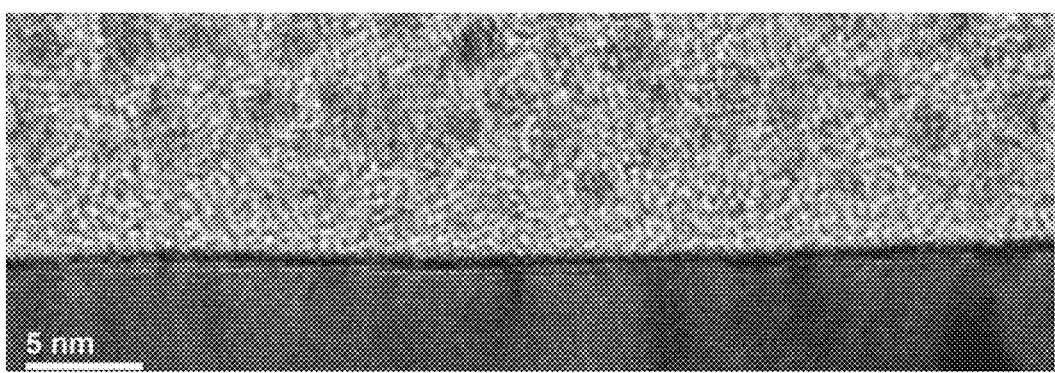
FIG. 13 A cross-sectional TEM image of the composite (PtNSXP) with substrate of the present invention prepared in Example 13.

A mesh-like gold substrate (12×14 mm, 100 mesh) was immersed for 5 minutes in piranha solution prepared from concentrated sulfuric acid (4.71 g), $Na_2S_2O_8$ (4.01 g), and ice (16.9 g); washed with water and ethanol; and dried under reduced pressure, yielding a gold substrate to which sulfur (S) had bonded or adsorbed. The gold substrate to which sulfur (S) had bonded or adsorbed that was obtained was stirred for 12 hours at 135° C. in a p-xylene solution (3 mL) of platinum acetate $(Pt(OAc)_2)$ (6.2 mg). The substrate obtained was thoroughly washed with a solution comprised of p-xylene. Subsequently, the substrate was dried for 30 minutes under reduced pressure, yielding the composite with substrate (PtNSXP) of the present invention. FIG. 13 shows a cross-sectional TEM image of the composite with substrate of the present invention obtained above. Based on these results, platinum nanoparticles (PtN) with a longer axis ranging from 2 to 5 nm were found to have been dispersed in a carbon layer and sulfur was found to be present accompanying to the platinum nanoparticles.

Example 14

<Synthesis Reaction Employing Catalyst Precursor>

The mesh-like composite with substrate (PtNSXP=catalyst precursor) (12×14 mm) of the present invention that had been prepared in Example 14 was added to a xylene (1 mL) solution of aniline (47.6 mg) and diisopropylamine (102.2 mg) and the mixture was heated at 135° C. for 12 hours. The reaction solution was then cooled to room temperature and the catalyst precursor was removed from the reaction solution. The fact that the targeted N-isopropylaniline was the only product in the reaction solution was confirmed by thin-layer chromatography and high-performance liquid chromatography.

INDUSTRIAL APPLICABILITY

The present invention is useful in fields related to catalyst precursors and catalysts for coupling reactions.

The invention claimed is:

1. A method for manufacturing a coupling product comprising subjecting a plurality of organic compounds to a coupling reaction in a solution to obtain a coupling product with a composite in which catalytic metal nanoparticles are dispersed in a continuous phase comprised of a polymer having a phenylene group unit and an alkylene group unit, the alkylene group having a number of carbon atoms ranging from 2 to 6, wherein the alkylene group unit is bonded to the phenylene group unit in at least positions 1 and 4, and wherein at least a portion of the catalytic metal nanoparticles has a particle diameter of not more than 20 nm or a composite structure comprising a substrate wherein the composite is provided on at least a portion of a surface of the substrate, and wherein the catalytic metal nanoparticles dispersed in the continuous phase partially elute into the solution of the coupling reaction.

2. The manufacturing method according to claim 1, wherein the coupling reaction employs a halogenated hydrocarbon as at least a portion of the starting material or as an additive.

3. The manufacturing method according to claim 1, wherein the coupling reaction is a carbon-carbon bond-forming reaction or a carbon-nitrogen bond-forming reaction.

4. The method according to claim 1, wherein a polymer has a sulfate group cross-linkage present between alkylene group units.

5. The method according to claim 4, wherein a content of the sulfate group cross-linkage falls within a range of 0.0001 to 0.1 as a molar ratio with the alkylene group unit.

6. The method according to claim 1, wherein a number of carbon atoms in the alkylene group unit ranges from 2 to 4.

7. The method according to claim 1, wherein the alkylene group unit is bonded to the phenylene group unit at positions 1, 2, and 4, or at positions 1, 2, 4, and 5.

8. The method according to claim 1, wherein a ratio of a mass of a continuous phase comprised of the polymer to a mass of the catalytic metal nanoparticles ranges from 100:0.1 to 100:10.

9. The method according to claim 1, wherein a catalytic metal constituting the catalytic metal nanoparticles is at least one metal selected from the group consisting of iron, nickel, cobalt, ruthenium, rhodium, palladium, iridium, platinum, and gold.

10. The method according to claim 1, wherein the catalytic metal nanoparticles are Pd nanoparticles at least a portion of which has a particle diameter falling within a range of 2 to 10 nm.

11. The method according to claim 1, wherein the catalytic metal nanoparticles are Ni nanoparticles at least a portion of which has a particle diameter falling within a range of 5 to 20 nm.

12. A method of using a composite or a composite structure as a catalyst, or catalyst precursor, for a coupling reaction, wherein the composite comprises catalytic metal nanoparticles dispersed in a continuous phase comprised of a polymer having a phenylene group unit and an alkylene group unit, the alkylene group having a number of carbon atoms ranging from 2 to 6, wherein the alkylene group unit is bonded to the phenylene group unit in at least positions 1 and 4, and wherein at least a portion of the catalytic metal nanoparticles has a particle diameter of not more than 20 nm; and wherein the composite structure comprises a substrate and the composite provided on at least a portion of a surface of the substrate.

13. The method according to claim 12, wherein the coupling reaction employs a halogenated hydrocarbon as at least a portion of a starting material or as an additive.

14. The method according to claim 12, wherein the coupling reaction is a carbon-carbon bond-forming reaction or a carbon-nitrogen bond-forming reaction.

15. The method according to claim 12, wherein the polymer has a sulfate group cross-linkage present between alkylene group units.

16. The method according to claim 15, wherein a content of the sulfate group cross-linkage falls within a range of 0.0001 to 0.1 as a molar ratio with the alkylene group unit.

17. The method according to claim 12, wherein a number of carbon atoms in the alkylene group unit ranges from 2 to 4.

18. The method according to claim 12, wherein the alkylene group unit is bonded to the phenylene group unit at positions 1, 2, and 4, or at positions 1, 2, 4, and 5.

19. The method according to claim 12, wherein a ratio of a mass of the continuous phase comprised of the polymer to a mass of the catalytic metal nanoparticles ranges from 100:0.1 to 100:10.

20. The method according to claim 12, wherein a catalytic metal constituting the catalytic metal nanoparticles is at least one metal selected from the group consisting of iron, nickel, cobalt, ruthenium, rhodium, palladium, iridium, platinum, and gold.

* * * * *